US012693280B2

(12) United States Patent
Lee et al.

(10) Patent No.: US 12,693,280 B2
(45) Date of Patent: Jul. 28, 2026

(54) DEVICE FOR MEASURING ODOR AND METHOD FOR MEASURING ODOR USING THE SAME

(71) Applicants:Hyundai Motor Company, Seoul (KR); Kia Corporation, Seoul (KR)

(72) Inventors: Tae Hee Lee, Yongin-si (KR); Dae Un Sung, Incheon (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 381 days.

(21) Appl. No.: 18/479,248

(22) Filed: Oct. 2, 2023

(65) Prior Publication Data

US 2024/0361286 A1 Oct. 31, 2024

(30) Foreign Application Priority Data

Apr. 28, 2023 (KR) ........................ 10-2023-0055861

(51) Int. Cl.
*G01N 33/00* (2006.01)

(52) U.S. Cl.
CPC ..... *G01N 33/0016* (2013.01); *G01N 33/0073* (2013.01)

(58) Field of Classification Search
CPC .......... G01N 33/0016; G01N 33/0073; G01N 33/0047; G01N 33/0001; G01D 21/02
See application file for complete search history.

(56) References Cited

U.S. PATENT DOCUMENTS

| | | | | |
|---|---|---|---|---|
| 6,488,635 B1 * | 12/2002 | Mottram | ................ | A61B 5/097 |
| | | | | 119/14.01 |
| 2003/0108432 A1 * | 6/2003 | Kawaguchi | ......... | F04B 27/1804 |
| | | | | 417/222.2 |
| 2009/0277603 A1 * | 11/2009 | Yang | ........................ | F24V 50/00 |
| | | | | 165/45 |
| 2021/0190747 A1 | 6/2021 | Cobley et al. | | |

FOREIGN PATENT DOCUMENTS

| | | | | | |
|---|---|---|---|---|---|
| CN | 102494932 | A | | 6/2012 | |
| CN | 107587417 | A | * | 1/2018 | |
| CN | 107654362 | A | * | 2/2018 | .............. F04B 51/00 |
| CN | 112394145 | A | | 2/2021 | |
| CN | 118148903 | A | * | 6/2024 | .............. F04B 53/22 |
| JP | 2003307473 | A | | 10/2003 | |
| JP | 2006118462 | A | * | 5/2006 | .............. F04B 27/14 |
| WO | 9700444 | A1 | | 1/1997 | |
| WO | 2016078217 | A1 | | 5/2016 | |

* cited by examiner

*Primary Examiner* — Francis C Gray
(74) *Attorney, Agent, or Firm* — Slater Matsil, LLP

(57) ABSTRACT

An embodiment device for measuring an odor includes a prechamber including an inlet and an outlet, a flow guide pipe disposed in the prechamber and connected between the inlet and the outlet in a predetermined pattern to allow air containing the odor to flow therethrough, a first sensor mounted to the inlet that measures a temperature and a humidity of the air entering the flow guide pipe, a second sensor mounted to the outlet that measures the temperature and the humidity of the air discharged from the flow guide pipe, a first temperature/humidity controller mounted to the prechamber that adjusts the temperature and the humidity of the air flowing through the flow guide pipe, an odor sensor chamber connected to the outlet, and an odor sensor mounted in the odor sensor chamber that senses the odor contained in the air discharged from the flow guide pipe.

20 Claims, 5 Drawing Sheets

FIG. 6

DEVICE FOR MEASURING ODOR AND METHOD FOR MEASURING ODOR USING THE SAME

CROSS-REFERENCE TO RELATED APPLICATIONS

This application claims the benefit of Korean Patent Application No. 10-2023-0055861, filed on Apr. 28, 2023, which application is hereby incorporated herein by reference.

TECHNICAL FIELD

The present disclosure relates to a device and method for measuring odor.

BACKGROUND

As is well known, inherent odors and volatile organic compound (VOC) odors generated from various interior parts of vehicles, such as seat covers, head linings, door trims, and mats, are major causes of complaints about new vehicles.

In addition, an odor due to mold propagation caused by moisture condensed in an evaporator core during operation of an air-conditioner of a vehicle also causes discomfort to vehicle users.

In addition, various kinds of odors may be included in external air flowing into vehicles during travel depending on the surrounding environment, and the odors introduced into vehicles from outside may also give vehicle users an unpleasant feeling.

The emotional quality of vehicles may be degraded due to various kinds of odors generated in the vehicles or introduced thereinto from outside.

Therefore, accurate odor sensing of an odor sensor and construction of odor data are required in order to analyze causes of various kinds of odors generated in vehicles or introduced thereinto from outside and to remove the odors. In addition, it is necessary to analyze the components of various kinds of odors generated in vehicles or introduced thereinto from outside and concentrations of the odor components in order to clearly identify actual causes of the odors.

In addition, in order to settle civil complaints related to odors generated in various industrial sites as well as in vehicles, it is necessary to accurately measure the components of odors and concentrations of the odor components by installing odor sensors in the corresponding industrial sites.

To this end, as conventional odor sensors for measuring odors generated in various industrial sites as well as in vehicles, electrochemical odor sensors or electrochemical odor sensor arrays may be used. Alternatively, odor biosensors, such as biopeptide-type sensors or sensors using amino acids, may be used.

However, electrochemical odor sensors have a limitation in being used as odor sensors for vehicles due to the low sensing accuracy, the low durability, and the very short lifespan thereof. Biopeptide-type sensors or sensors using amino acids are sensors that change in color in response to specific odor components and concentrations thereof, and have an advantage of precise sensing response. However, biopeptide-type sensors or sensors using amino acids are very sensitive to ambient temperature and humidity. Therefore, there is a limitation in accurately measuring odor data.

Furthermore, odor data that is measured by the conventional odor sensors may be acquired at predetermined measurement time intervals. However, odor components are not uniformly distributed in the air during a predetermined time period, and odor data that is measured by the conventional odor sensors may change depending on the temperature and humidity of air or gas containing odor. Therefore, the measurement accuracy of the conventional odor sensors may be degraded.

For example, the conventional odor sensors may erroneously recognize water molecules as odor particles depending on the temperature and humidity of air or gas containing odor. Therefore, an error may occur in the measured odor data, and the accuracy of the measured odor data may be degraded.

The above information disclosed in this background section is only for enhancement of understanding of the background of embodiments of the invention, and therefore it may contain information that does not form the related art that is already known to a person of ordinary skill in the art.

SUMMARY

The present disclosure relates to a device and method for measuring odor. Particular embodiments relate to an odor measurement device and method capable of improving the measurement accuracy of an odor sensor by maintaining constant temperature and humidity of air flowing toward the odor sensor.

Embodiments of the present invention can solve problems associated with the related art, and embodiments of the present invention provide a device and method for measuring an odor, in which the temperature and humidity of air containing the odor are adjusted to predetermined levels using a prechamber equipped with a heater and a cooler, and thereafter, the air adjusted in temperature and humidity is supplied to an odor sensor chamber in which an odor sensor is disposed, thereby preventing the occurrence of an error in data on the odor measured by the odor sensor and obtaining highly accurate odor data.

One embodiment of the present invention provides a device for measuring odor, the device including a prechamber including an inlet and an outlet formed in respective end portions thereof, a flow guide pipe disposed in the prechamber so as to be connected between the inlet and the outlet in a predetermined pattern to allow air containing odor to flow therethrough, a first sensor mounted to the inlet to measure the temperature and humidity of the air entering the flow guide pipe, a second sensor mounted to the outlet to measure the temperature and humidity of the air discharged from the flow guide pipe, a first temperature/humidity controller mounted to the prechamber to adjust the temperature and humidity of the air flowing through the flow guide pipe, at least one odor sensor chamber connected to the outlet via a connection pipe, and an odor sensor mounted in the at least one odor sensor chamber to sense odor contained in the air escaping from the flow guide pipe.

In a preferred embodiment, the device for measuring odor may further include a controller configured to determine a need for a heating operation or a cooling operation of the first temperature/humidity controller based on the temperature and humidity of the air measured by the first sensor and the temperature and humidity of the air measured by the second sensor.

In another preferred embodiment, the controller may be configured to control the first temperature/humidity controller to perform a heating operation upon determining that the temperature of the air measured by the first sensor is less than a reference value or the humidity of the air measured by the first sensor is equal to or greater than a reference value and to control the first temperature/humidity controller to perform a cooling operation upon determining that the temperature of the air measured by the first sensor is equal to or greater than the reference value or the humidity of the air measured by the first sensor is less than the reference value.

In still another preferred embodiment, the controller may be configured to control the first temperature/humidity controller to stop the heating operation or the cooling operation upon determining that the temperature and humidity of the air measured by the second sensor have reached reference values.

In yet another preferred embodiment, the first temperature/humidity controller may include a first heater mounted to the prechamber to heat the air flowing through the flow guide pipe in order to adjust the temperature and humidity of the air and a first cooler mounted to the prechamber to cool the air flowing through the flow guide pipe in order to adjust the temperature and humidity of the air.

In still yet another preferred embodiment, the first temperature/humidity controller may be a Peltier element mounted to the prechamber to heat or cool the air flowing through the flow guide pipe in order to adjust the temperature and humidity of the air.

In a further preferred embodiment, the predetermined pattern of the flow guide pipe connected between the inlet and the outlet may be one of a helical pattern, a zigzag pattern, and a spiral pattern in order to secure a heating time or a cooling time for adjustment of the temperature and humidity of the air.

In another further preferred embodiment, the flow guide pipe may include a first flow guide pipe and a second flow guide pipe, and the first flow guide pipe and the second flow guide pipe may be independently connected between the inlet and the outlet in order to secure a heating time or a cooling time for adjustment of the temperature and humidity of the air.

In still another further preferred embodiment, the device for measuring odor may further include a second temperature/humidity controller mounted to the at least one odor sensor chamber to adjust the temperature and humidity of the air introduced into the at least one odor sensor chamber in response to a control signal of the controller.

In yet another further preferred embodiment, the controller may be configured to control the second temperature/humidity controller to perform a heating operation or a cooling operation upon determining that the temperature and humidity of the air measured by the second sensor have not reached reference values.

In still yet another further preferred embodiment, the second temperature/humidity controller may include a second heater mounted to the at least one odor sensor chamber to heat the air introduced into the at least one odor sensor chamber in order to adjust the temperature and humidity of the air in response to a control signal of the controller and a second cooler mounted to the at least one odor sensor chamber to cool the air introduced into the at least one odor sensor chamber in order to adjust the temperature and humidity of the air in response to a control signal of the controller.

In a still further preferred embodiment, the at least one odor sensor chamber may include a first odor sensor chamber and a second odor sensor chamber, and the first odor sensor chamber and the second odor sensor chamber may be connected to the outlet via branch pipes.

Another embodiment of the present invention provides a method of measuring odor, the method including causing air containing odor to flow to a flow guide pipe connected between an inlet and an outlet of a prechamber, measuring, by a first sensor mounted to the inlet and a second sensor mounted to the outlet, the temperature and humidity of the air, controlling, by a controller, a first temperature/humidity controller mounted to the prechamber to perform a heating operation or a cooling operation based on the temperature and humidity of the air measured by each of the first sensor and the second sensor, adjusting the temperature and humidity of the air flowing through the flow guide pipe to reference values through the heating operation or the cooling operation of the first temperature/humidity controller, supplying the air adjusted in temperature and humidity to the interior of an odor sensor chamber connected to the outlet, and sensing, by an odor sensor mounted in the odor sensor chamber, the odor contained in the air introduced into the odor sensor chamber.

In a preferred embodiment, the controller may control the first temperature/humidity controller to perform the heating operation upon determining that the temperature of the air measured by the first sensor is less than a reference value or the humidity of the air measured by the first sensor is equal to or greater than a reference value.

In another preferred embodiment, the controller may control the first temperature/humidity controller to perform the cooling operation upon determining that the temperature of the air measured by the first sensor is equal to or greater than the reference value or the humidity of the air measured by the first sensor is less than the reference value.

In still another preferred embodiment, the method of measuring odor may further include controlling, by the controller, the first temperature/humidity controller to stop the heating operation or the cooling operation upon determining that the temperature and humidity of the air measured by the second sensor have reached reference values.

In yet another preferred embodiment, the method of measuring odor may further include controlling, by the controller, a second temperature/humidity controller mounted to the odor sensor chamber to perform the heating operation or the cooling operation upon determining that the temperature and humidity of the air measured by the second sensor have not reached the reference values.

Other aspects of preferred embodiments of the invention are discussed infra.

The above and other features of embodiments of the invention are discussed infra.

BRIEF DESCRIPTION OF THE DRAWINGS

The above and other features of embodiments of the present invention will now be described in detail with reference to certain exemplary embodiments thereof illustrated in the accompanying drawings which are given hereinbelow by way of illustration only, and thus are not limitative of the embodiments of the present invention, and wherein:

FIG. 6 is a schematic diagram showing the device for measuring odor according to embodiments of the present invention in which a second temperature/humidity controller is mounted to an odor sensor chamber.

Figure 1A:
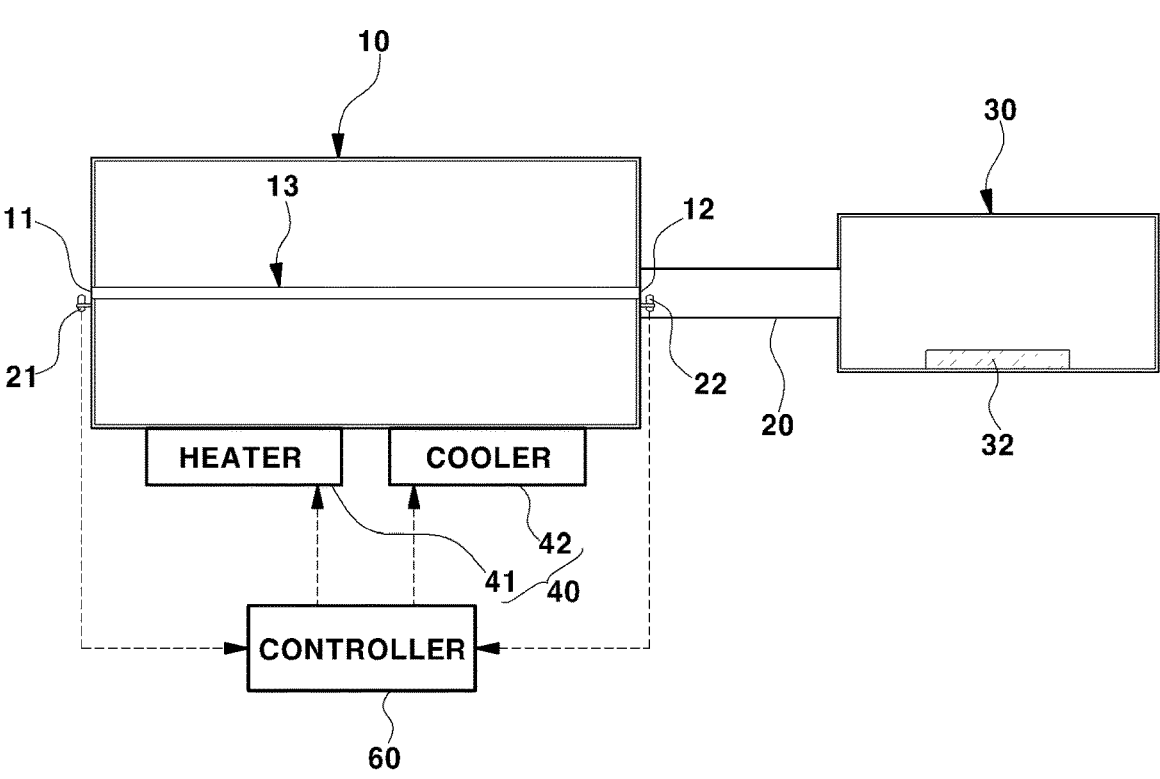
FIG. 1A is a schematic diagram showing a device for measuring odor according to embodiments of the present invention.

It should be understood that the appended drawings are not necessarily to scale, presenting a somewhat simplified representation of various preferred features illustrative of the basic principles of embodiments of the invention. The specific design features of embodiments of the present invention as disclosed herein, including, for example, specific dimensions, orientations, locations, and shapes, will be determined in part by the particular intended application and use environment.

In the figures, reference numbers refer to the same or equivalent parts of embodiments of the present invention throughout the several figures of the drawings.

DETAILED DESCRIPTION OF ILLUSTRATIVE EMBODIMENTS

Various exemplary embodiments will now be described more fully with reference to the accompanying drawings, in which only some exemplary embodiments are shown. Specific structural and functional details disclosed herein are merely representative for the purpose of describing exemplary embodiments. Embodiments of the present invention, however, may be embodied in many alternate forms, and should not be construed as being limited only to the exemplary embodiments set forth herein. Accordingly, while exemplary embodiments of the invention are capable of being variously modified and taking alternative forms, embodiments thereof are shown by way of example in the drawings and will herein be described in detail. It should be understood, however, that there is no intent to limit the embodiments of the present invention to the particular exemplary embodiments disclosed. On the contrary, exemplary embodiments are to cover all modifications, equivalents, and alternatives falling within the scope of the invention.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of the exemplary embodiments of the present invention.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

Wherever possible, the same reference numbers will be used throughout the drawings to refer to the same or like parts. The terminology used herein is for the purpose of describing particular embodiments only and is not intended to be limiting of exemplary embodiments of the invention. As used herein, the singular forms "a", "an", and "the" are intended to include the plural forms as well, unless the context clearly indicates otherwise. It will be further understood that the terms "comprises", "comprising", "includes", and/or "including", when used herein, specify the presence of stated components, steps, operations, and/or elements, but do not preclude the presence or addition of one or more other components, steps, operations, and/or elements.

Hereinafter, exemplary embodiments of the present invention will be described in detail with reference to the accompanying drawings.

Figure 1B:
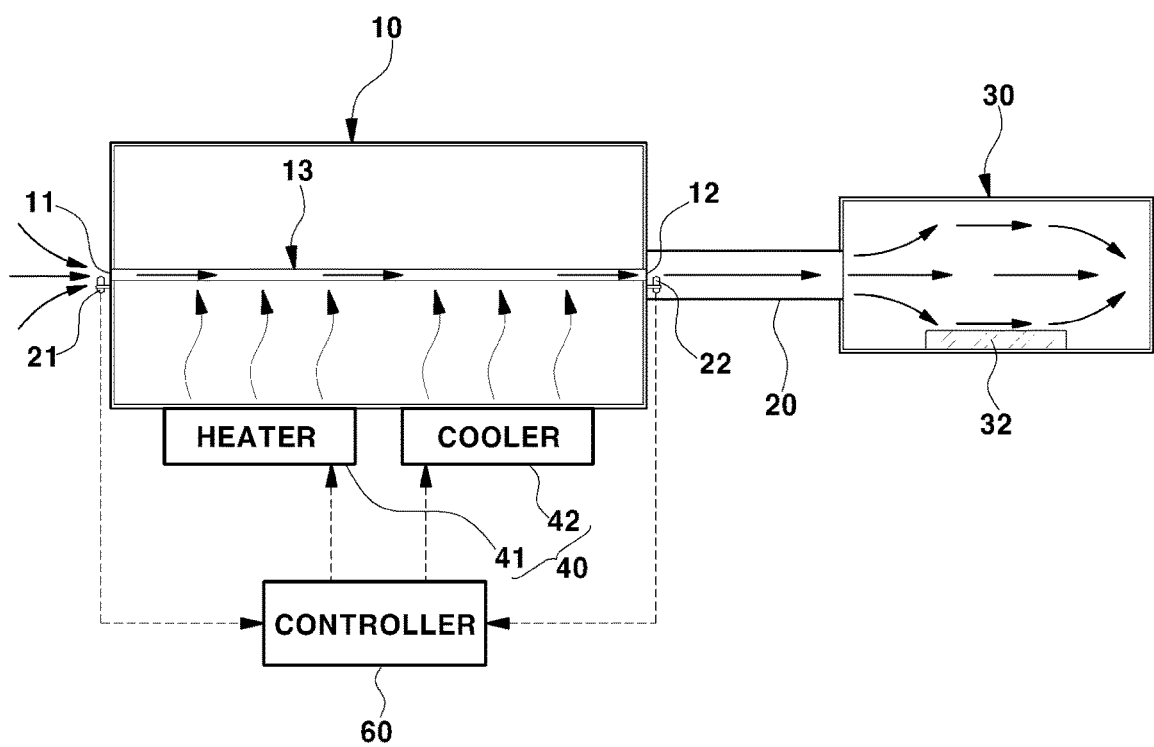
FIG. 1B is a schematic diagram showing flow of air containing odor in the device for measuring odor according to embodiments of the present invention.

FIGS. 1A and 1B are schematic diagrams showing a device for measuring odor according to embodiments of the present invention. Reference numeral 10 denotes a prechamber, and reference numeral 30 denotes an odor sensor chamber.

The prechamber 10 and the odor sensor chamber 30 are connected to each other via a connection pipe 20 so as to communicate with each other.

The prechamber 10 may be manufactured in a structure in which a fluid, an odor of which is to be measured, i.e., air containing an odor, is adjusted in temperature and humidity while flowing through the prechamber 10 before entering the odor sensor chamber 30 through the connection pipe 20.

To this end, the prechamber 10 includes an inlet 11 formed in one end portion thereof to introduce air thereinto, an outlet 12 formed in the other end portion thereof to discharge the air, adjusted in temperature and humidity, therefrom, and a flow guide pipe 13 connected between the inlet 11 and the outlet 12 to guide the air to flow from the inlet 11 to the outlet 12.

In addition, a first sensor 21, which is a temperature/humidity sensor, is attached to the inlet 11 of the prechamber 10 in order to measure the temperature and humidity of the air entering the flow guide pipe 13, and a second sensor 22, which is a temperature/humidity sensor, is attached to the outlet 12 of the prechamber 10 in order to measure the temperature and humidity of the air escaping from the flow guide pipe 13.

In addition, a first temperature/humidity controller 40, which heats or cools the air flowing through the flow guide pipe 13, is mounted to the prechamber 10 in order to adjust the temperature and humidity of the air flowing through the flow guide pipe 13.

The first temperature/humidity controller 40 may include a first heater 41 and a first cooler 42, which are mounted parallel to each other on the lower side of the prechamber 10.

For example, the first heater 41 may be implemented as a heat coil, and the first cooler 42 may be implemented as a blower configured to blow cool air, generated by operation of an air-conditioner of a vehicle, to the interior of the prechamber 10.

The device for measuring odor according to embodiments of the present invention further includes a controller 60, which receives signals indicative of the temperature and humidity of the air measured by the first sensor 21 and signals indicative of the temperature and humidity of the air measured by the second sensor 22 and determines a need for a heating operation or a cooling operation of the first temperature/humidity controller 40.

Upon determining that the temperature of the air measured by the first sensor 21 is less than a reference value or the humidity of the air measured by the first sensor 21 is equal to or greater than a reference value, the controller 60 controls the first heater 41 of the first temperature/humidity controller 40 to perform a heating operation. Upon determining that the temperature of the air measured by the first sensor 21 is equal to or greater than the reference value or the humidity of the air measured by the first sensor 21 is less than the reference value, the controller 60 controls the first cooler 42 of the first temperature/humidity controller 40 to perform a cooling operation.

In addition, upon determining that the temperature and humidity of the air measured by the second sensor 22 (e.g., the air adjusted in temperature and humidity by operation of the first heater 41 or operation of the first cooler 42 while flowing through the flow guide pipe 13) have reached the reference values, the controller 60 controls the first heater 41 or the first cooler 42 of the first temperature/humidity controller 40 to stop operation.

In this case, the reference value for the temperature of the air and the reference value for the humidity of the air may be defined as room temperature and humidity at room temperature, respectively.

When the first heater 41 performs a heating operation under the control of the controller 60, the air flowing through the flow guide pipe 13 may be heated to be adjusted in temperature and humidity. Alternatively, when the first cooler 42 performs a cooling operation under the control of the controller 60, the air flowing through the flow guide pipe 13 may be cooled to be adjusted in temperature and humidity.

In detail, heat generated by the heating operation of the first heater 41 may be transferred to the flow guide pipe 13 via the inner space in the prechamber 10, whereby the temperature of the air in the flow guide pipe 13 may be increased, and the humidity thereof may be lowered. Alternatively, cooling air generated by the cooling operation of the first cooler 42 may be brought into contact with the flow guide pipe 13 via the inner space in the prechamber 10, whereby the temperature of the air in the flow guide pipe 13 may be lowered, and the humidity thereof may be increased.

Figure 4:
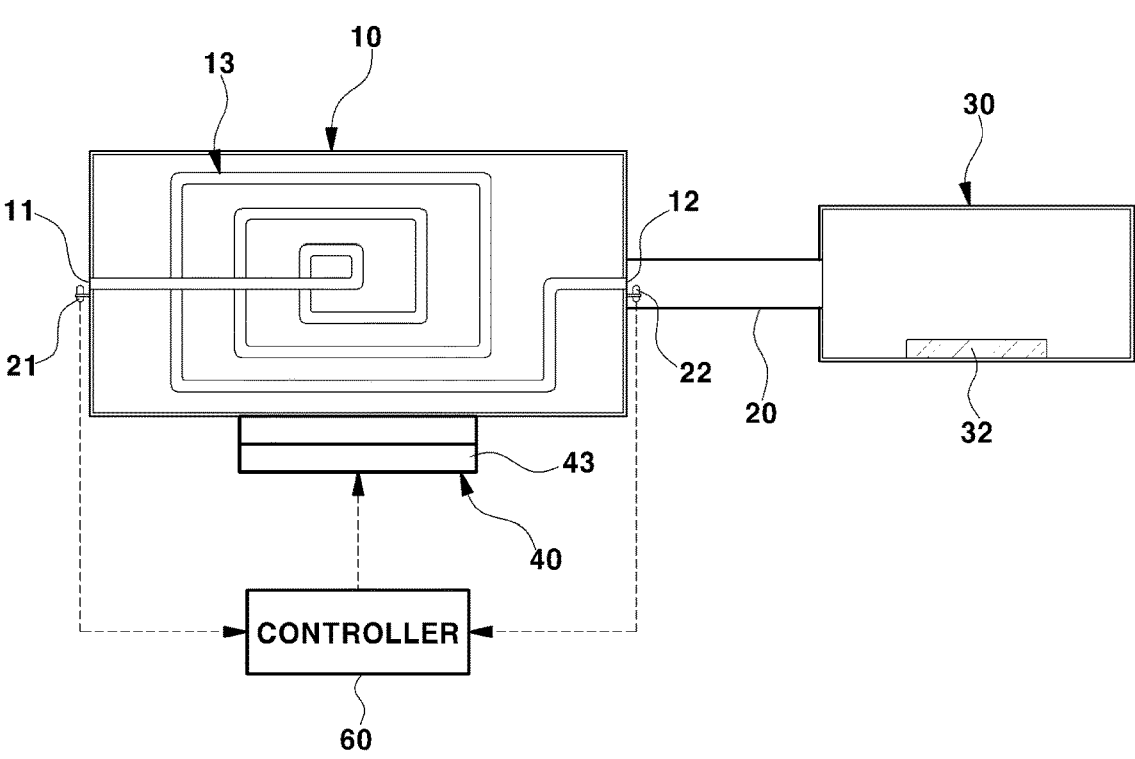
FIG. 4 is a schematic diagram showing the device for measuring odor according to embodiments of the present invention equipped with a spiral-shaped flow guide pipe.

Alternatively, as shown in FIG. 4, the first temperature/humidity controller 40 may be implemented as a Peltier element 43, which is mounted to the prechamber 10 and performs a heating or cooling operation in order to adjust the temperature and humidity of the air flowing through the flow guide pipe 13.

As is well known, the Peltier element is a thermoelectric element characterized in that, according to electrical current control, one surface thereof emits heat to realize heating and the other surface thereof absorbs heat to realize cooling or one surface thereof absorbs heat to realize cooling and the other surface thereof emits heat to realize heating.

Accordingly, when the Peltier element 43 performs a heating operation of emitting heat according to the current control of the controller 60, the temperature of the air in the flow guide pipe 13 may be increased, and the humidity thereof may be lowered. Alternatively, when the Peltier element 43 performs a cooling operation of absorbing heat according to the current control of the controller 60, the temperature of the air in the flow guide pipe 13 may be lowered, and the humidity thereof may be increased.

Figure 2:
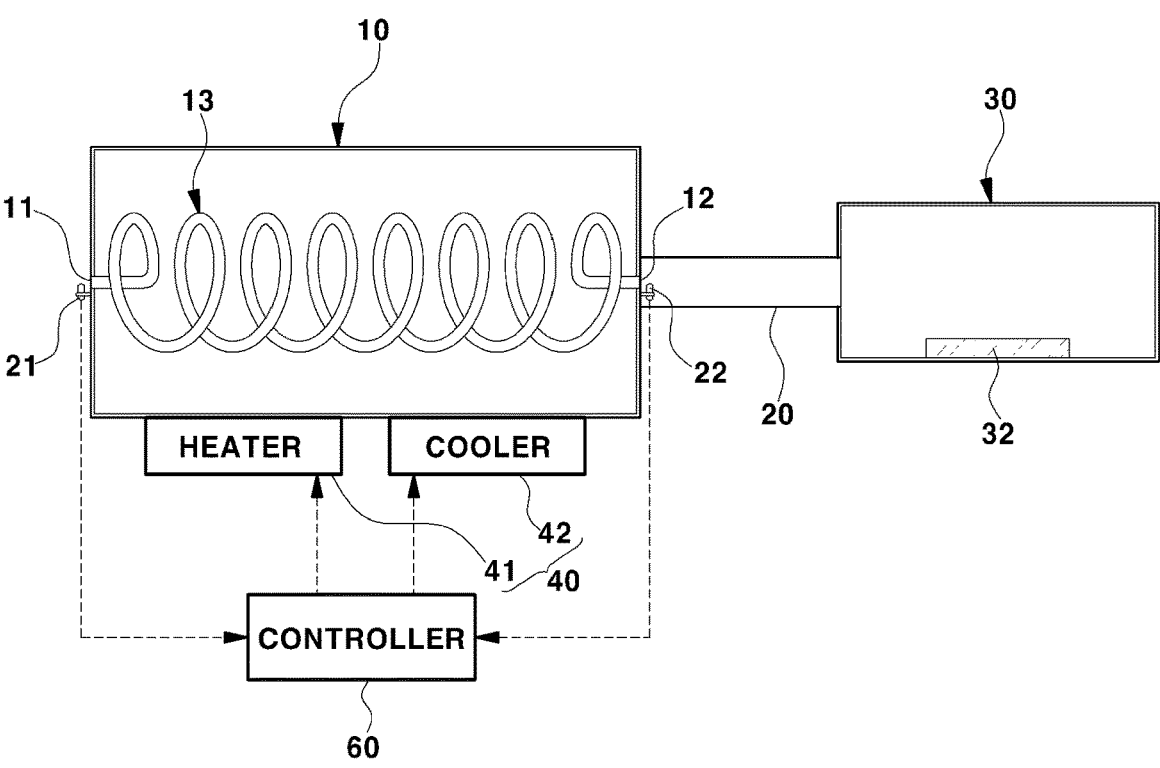
FIG. 2 is a schematic diagram showing the device for measuring odor according to embodiments of the present invention equipped with a helical-shaped flow guide pipe.
Figure 3:
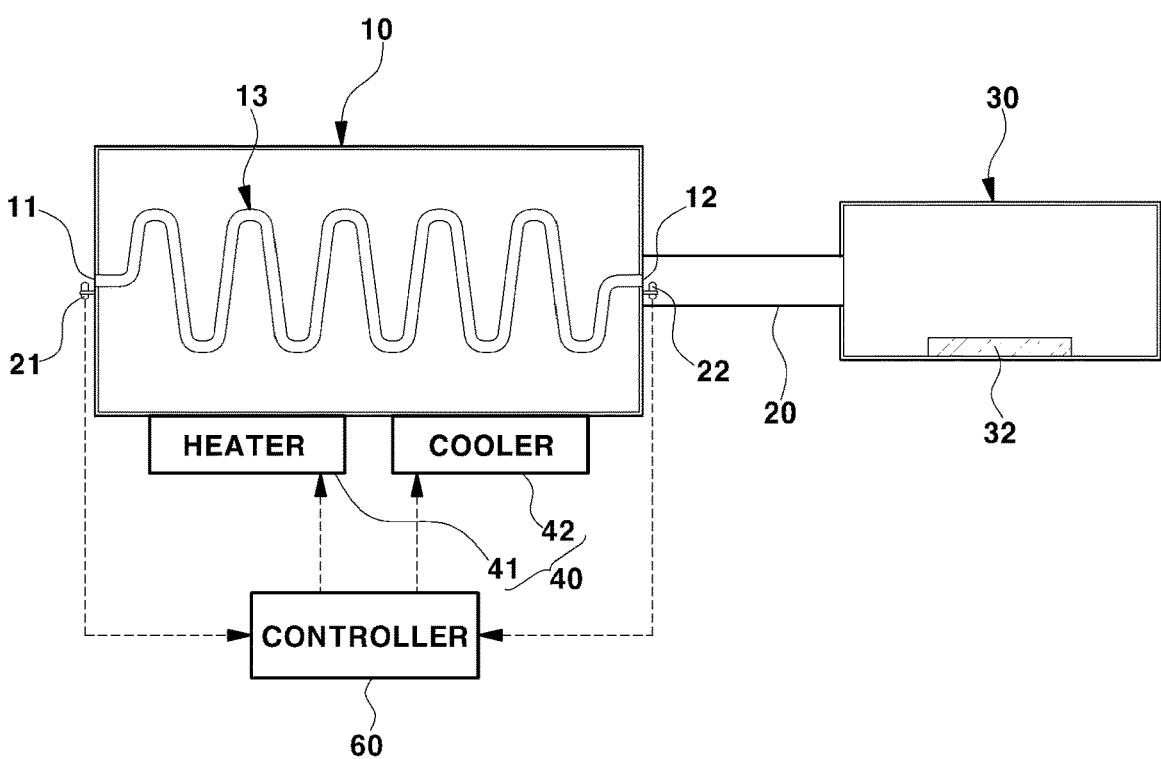
FIG. 3 is a schematic diagram showing the device for measuring odor according to embodiments of the present invention equipped with a zigzag-shaped flow guide pipe.

In order to secure a time for heating or cooling of the air in the flow guide pipe 13, that is, in order to secure a heating or cooling time for smooth adjustment of the temperature and humidity of the air to target values, the flow guide pipe 13 may be connected between the inlet 11 and the outlet 12 of the prechamber 10 in a helical pattern, as shown in FIG. 2. Alternatively, as shown in FIG. 3, the flow guide pipe 13 may be connected between the inlet 11 and the outlet 12 of the prechamber 10 in a zigzag pattern. Alternatively, as shown in FIG. 4, the flow guide pipe 13 may be connected between the inlet 11 and the outlet 12 of the prechamber 10 in a spiral pattern.

Figure 5:
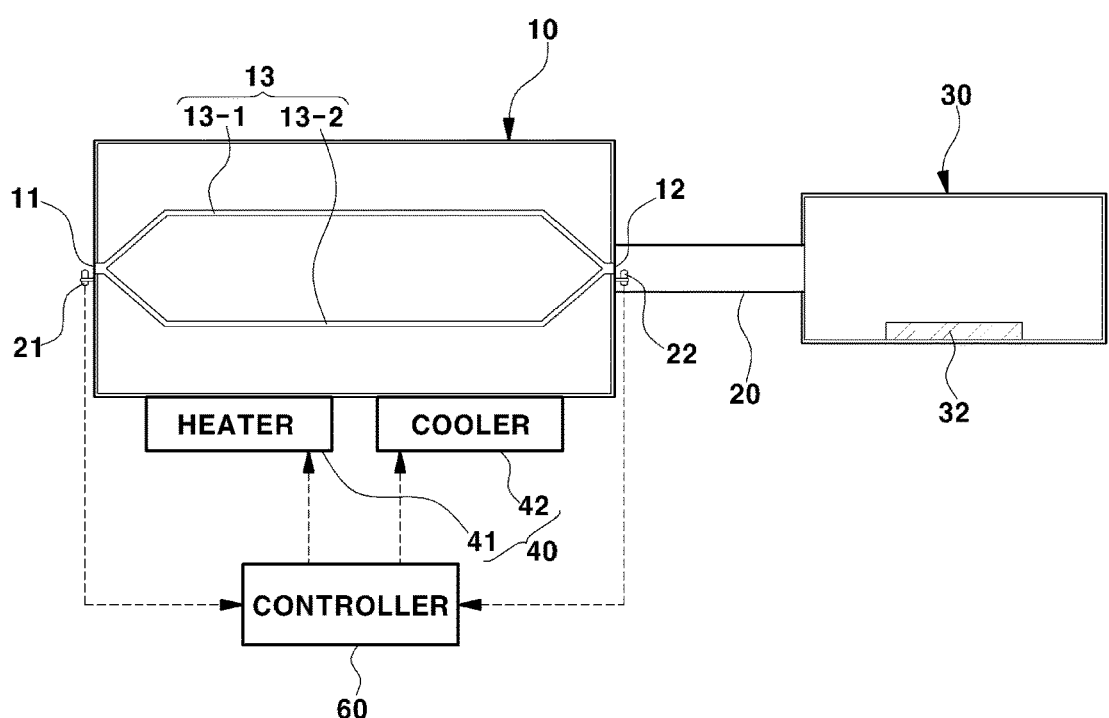
FIG. 5 is a schematic diagram showing the device for measuring odor according to embodiments of the present invention in which a flow guide pipe includes a first flow guide pipe and a second flow guide pipe.

Alternatively, in order to secure a time for heating or cooling of the air in the flow guide pipe 13, that is, in order to secure a heating or cooling time for smooth adjustment of the temperature and humidity of the air to target values, the flow guide pipe 13 may include a first flow guide pipe 13-1 and a second flow guide pipe 13-2, which are independently connected between the inlet 11 and the outlet 12 of the prechamber 10, as shown in FIG. 5.

At least one odor sensor 32 may be mounted in the odor sensor chamber 30, which is connected to the prechamber 10 via the connection pipe 20 so as to communicate with the prechamber 10. The odor sensor 32 may be an electrochemical odor sensor, an electrochemical odor sensor array, or an odor biosensor, such as a biopeptide-type sensor or a sensor using amino acids.

Figure 7:
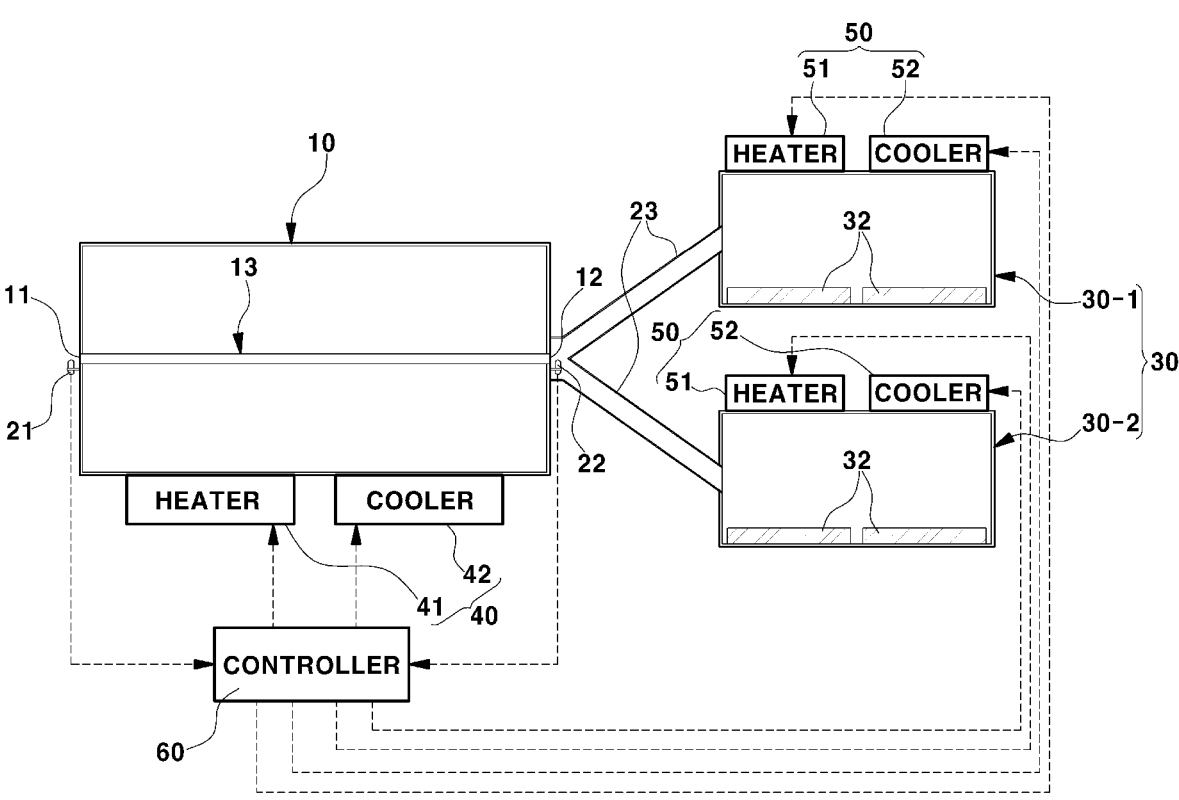
FIG. 7 is a schematic diagram showing the device for measuring odor according to embodiments of the present invention in which the odor sensor chamber includes a first odor sensor chamber and a second odor sensor chamber.

When the number of odor sensors 32 to be mounted in the odor sensor chamber 30 is so large that all of the odor sensors 32 are not mounted in a single odor sensor chamber, or when the odor sensors 32 need to be classified into groups according to the type thereof and each group of odor sensors 32 needs to be mounted in an independent space, the odor sensor chamber 30 may include a first odor sensor chamber 30-1 and a second odor sensor chamber 30-2, which are independently connected to the outlet 12 of the prechamber 10 via respective branch pipes 23, as shown in FIG. 7.

Accordingly, each of the groups of odor sensors 32 classified according to the type thereof or according to a predetermined number thereof may be mounted in a respective one of the first odor sensor chamber 30-1 and the second odor sensor chamber 30-2.

When the air that has passed through the flow guide pipe 13, i.e., the air adjusted in temperature and humidity by the first temperature/humidity controller 40, enters the odor sensor chamber 30 through the connection pipe 20, the odor sensor 32 may easily sense odor contained in the air filling the odor sensor chamber 30.

In this way, the air containing odor is adjusted in temperature and humidity to predetermined levels, and then is supplied to the odor sensor chamber 30 in which the odor sensor 32 is disposed, whereby it is possible to prevent the occurrence of an error in data on the odor measured by the odor sensor 32 and to obtain highly accurate odor data.

Figure 6:
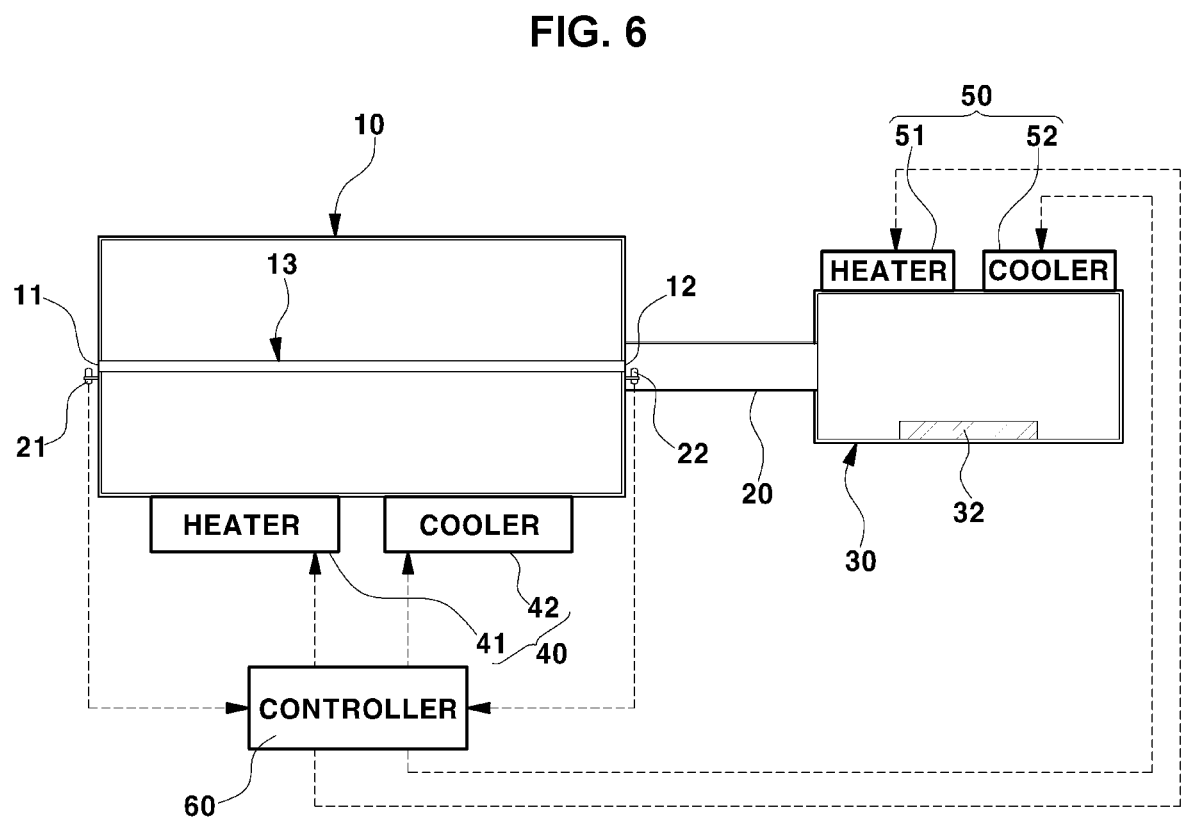

Meanwhile, as shown in FIGS. 6 and 7, the odor sensor chamber 30 may be further provided with a second temperature/humidity controller 50, which secondarily adjusts the temperature and humidity of the air introduced into the odor sensor chamber 30 in response to a control signal of the controller 60.

The second temperature/humidity controller 50 may include a second heater 51 and a second cooler 52, which are mounted parallel to each other on a predetermined portion of the odor sensor chamber 30.

Similarly, the second heater 51 may be implemented as a heat coil, and the second cooler 52 may be implemented as a blower configured to blow cool air, generated by operation of an air-conditioner of a vehicle, to the interior of the odor sensor chamber 30.

Upon determining that the temperature and humidity of the air measured by the second sensor 22 have not reached the reference values, the controller 60 may perform current control such that the second heater 51 of the second temperature/humidity controller 50 performs a heating operation or the second cooler 52 thereof performs a cooling operation.

In detail, when the temperature and humidity of the air measured by the second sensor 22 do not reach the reference values, that is, when the air flowing through the flow guide pipe 13 is not adjusted in temperature and humidity to levels equivalent to the reference values by the first temperature/humidity controller 40, the temperature and humidity of the air introduced into the odor sensor chamber 30 may be secondarily adjusted by the heating operation of the second heater 51 in response to a control signal of the controller 60 or the cooling operation of the second cooler 52 in response to a control signal of the controller 60.

In this case, during operation of the second heater 51 or the second cooler 52 of the second temperature/humidity controller 50, the controller 60 may control the second heater 51 or the second cooler 52 to stop operation upon determining, based on a sensing signal received from the second sensor 22, that the temperature and humidity of the air measured by the second sensor 22 have reached the reference values.

As described above, when the temperature and humidity of the air introduced into the odor sensor chamber 30 do not satisfy the reference values, the temperature and humidity of the air in the odor sensor chamber 30 are secondarily adjusted to best satisfy the reference values by the heating or cooling operation of the second temperature/humidity controller 50. Accordingly, it is possible to prevent the occurrence of an error in data on the odor measured by the odor sensor 32 and to obtain highly accurate odor data.

Hereinafter, a method of measuring odor according to embodiments of the present invention using the above-described configuration will be described.

First, air containing odor may be introduced into the inlet 11 of the prechamber 10. For example, air containing various kinds of odors, generated inside and outside a vehicle or a future mobility vehicle (e.g., a purpose built vehicle (PBV) or an urban air mobility (UAM) vehicle), may be introduced into the inlet 11 of the prechamber 10.

The air containing odor, introduced into the inlet 11 of the prechamber 10, flows to the outlet 12 along the flow guide pipe 13.

In this case, the first sensor 21 mounted to the inlet 11 and the second sensor 22 mounted to the outlet 12 measure the temperature and humidity of the air and transmit signals indicative of the temperature and humidity of the air to the controller 60.

Subsequently, the controller 60 controls the first heater 41 or the first cooler 42 of the first temperature/humidity controller 40 to perform an operation based on the signals indicative of the temperature and humidity of the air measured by the first sensor 21 and the second sensor 22.

For example, upon determining that the temperature of the air measured by the first sensor 21 is less than a reference value or the humidity of the air measured by the first sensor 21 is equal to or greater than a reference value, the controller 60 controls the first heater 41 of the first temperature/ humidity controller 40 to perform a heating operation, thereby heating the air flowing through the flow guide pipe 13 in order to adjust the temperature and humidity of the air.

Alternatively, upon determining that the temperature of the air measured by the first sensor 21 is equal to or greater than the reference value or the humidity of the air measured by the first sensor 21 is less than the reference value, the controller 60 controls the first cooler 42 of the first temperature/humidity controller 40 to perform a cooling operation, thereby cooling the air flowing through the flow guide pipe 13 in order to adjust the temperature and humidity of the air.

Accordingly, heat generated by the heating operation of the first heater 41 is transferred to the flow guide pipe 13 via the inner space in the prechamber 10, whereby the temperature of the air in the flow guide pipe 13 may be increased, and the humidity thereof may be lowered. Alternatively, cooling air generated by the cooling operation of the first cooler 42 is brought into contact with the flow guide pipe 13 via the inner space in the prechamber 10, whereby the temperature of the air in the flow guide pipe 13 may be lowered, and the humidity thereof may be increased.

In this way, the temperature and humidity of the air flowing through the flow guide pipe 13 may be adjusted to the reference values (e.g., room temperature and humidity at room temperature) by the heating or cooling operation of the first temperature/humidity controller 40.

Subsequently, the controller 60 determines whether the temperature and humidity of the air flowing toward the odor sensor chamber 30 through the flow guide pipe 13 are adjusted to the reference values by the heating or cooling operation of the first temperature/humidity controller 40.

To this end, the controller 60 receives signals indicative of the temperature and humidity of the air measured by the second sensor 22. Upon determining, based on the received signals, that the temperature and humidity of the air measured by the second sensor 22 have reached the reference values, the controller 60 controls the first temperature/humidity controller 40 to stop the heating or cooling operation.

In more detail, upon determining that the temperature and humidity of the air measured by the second sensor 22 (e.g., the air adjusted in temperature and humidity by operation of the first heater 41 or operation of the first cooler 42 while flowing through the flow guide pipe 13) have reached the reference values, the controller 60 controls the first heater 41 or the first cooler 42 of the first temperature/humidity controller 40 to stop operation.

In this way, the temperature and humidity of the air flowing toward the odor sensor chamber 30 through the flow guide pipe 13 may be easily adjusted to the reference values (e.g., room temperature and humidity at room temperature).

Meanwhile, upon determining that the temperature and humidity of the air measured by the first sensor 21 or the second sensor 22 satisfy the reference values (e.g., room temperature and humidity at room temperature), the controller 60 performs control such that the temperature and humidity of the air flowing toward the odor sensor chamber 30 through the flow guide pipe 13 are not adjusted.

Subsequently, when the air adjusted in temperature and humidity is supplied to the odor sensor chamber 30, which is connected to the outlet 12 of the prechamber 10, the odor sensor 32 mounted in the odor sensor chamber 30 may easily sense odor contained in the air introduced into the odor sensor chamber 30.

In this case, upon determining, based on signals received from the second sensor 22, which indicate the temperature and humidity of the air measured by the second sensor 22, that the temperature and humidity of the air measured by the second sensor 22 have not reached the reference values, the controller 60 may control the second temperature/humidity controller 50 mounted to the odor sensor chamber 30 to perform a heating operation or a cooling operation.

In detail, when the temperature and humidity of the air measured by the second sensor 22 do not reach the reference values, that is, when the air flowing through the flow guide pipe 13 is not adjusted in temperature and humidity to levels equivalent to the reference values by the first temperature/ humidity controller 40, the temperature and humidity of the air introduced into the odor sensor chamber 30 may be secondarily adjusted by the heating operation of the second heater 51 in response to a control signal of the controller 60 or the cooling operation of the second cooler 52 in response to a control signal of the controller 60.

In this way, air containing odor is adjusted in temperature and humidity to predetermined levels and then is supplied to the odor sensor chamber 30 in which the odor sensor 32 is disposed, whereby it is possible to prevent the occurrence of an error in data on the odor measured by the odor sensor 32 and to obtain highly accurate odor data.

In particular, in the case in which the odor sensor is an odor biosensor, it is necessary to consider the fact that the sensing sensitivity and responsivity thereof vary depending on ambient temperature and humidity. However, in embodiments of the present invention, since air containing odor is adjusted in temperature and humidity to predetermined levels and then is supplied to the odor sensor chamber in which the odor biosensor is disposed, it is possible to prevent the odor biosensor from erroneously recognizing water molecules as odor particles, thus maintaining constant sensing sensitivity and responsivity of the odor biosensor. As a result, the measurement accuracy of the odor biosensor may be greatly improved.

The odor measurement device according to embodiments of the present invention may be mounted not only in vehicles but also in future mobility vehicles, such as purpose built vehicles (PBVs) or urban air mobility (UAM) vehicles, in order to measure various kinds of odors generated therein. Accordingly, it is possible to clearly analyze actual causes of odors based on the measured odor data and to improve emotional quality related to odors of various types of vehicles and future mobility vehicles.

In addition, the odor measurement device according to embodiments of the present invention may be mounted in robots designed to easily access various industrial sites (e.g., industrial sites in which gas leakage or odor leakage accidents occur), whereby the scope of function of the robots may be extended to a function of accurately measuring components of odors generated in various industrial sites and concentrations of the odor components.

As is apparent from the above description, embodiments of the present invention have the following effects.

First, air containing odor is adjusted in temperature and humidity to predetermined levels and then is supplied to an odor sensor chamber in which an odor sensor is disposed. Accordingly, it is possible to prevent the occurrence of an error in data on the odor measured by the odor sensor and to obtain highly accurate odor data.

In particular, in the case in which the odor sensor is an odor biosensor, it is necessary to consider the fact that the sensing sensitivity and responsivity thereof vary depending on ambient temperature and humidity. However, in embodiments of the present invention, air containing odor is adjusted in temperature and humidity to predetermined levels and then is supplied to the odor sensor chamber in which the odor biosensor is disposed. Accordingly, the odor biosensor may be prevented from erroneously recognizing water molecules as odor particles, and thus constant sensing sensitivity and responsivity of the odor biosensor may be maintained. As a result, the measurement accuracy of the odor biosensor may be greatly improved.

Second, the odor measurement device according to embodiments of the present invention may be mounted not only in vehicles but also in future mobility vehicles, such as PBVs or UAM vehicles, in order to measure various kinds of odors generated therein. Accordingly, it is possible to clearly analyze actual causes of odors based on the measured odor data and to improve emotional quality related to odors of various types of vehicles and future mobility vehicles.

Third, the odor measurement device according to embodiments of the present invention may be mounted in robots designed to easily access various industrial sites. Accordingly, the scope of function of the robots may be extended to a function of accurately measuring components of odors generated in various industrial sites and concentrations of the odor components.

Embodiments of the present invention have been described above with reference to exemplary embodiments. The embodiments described in the specification and shown in the accompanying drawings are illustrative only and are not intended to represent all aspects of embodiments of the invention. Therefore, embodiments of the present invention are not limited to the embodiments presented herein, and it is to be understood by those skilled in the art that various modifications or changes can be made without departing from the technical spirit or scope of the invention as disclosed in the appended claims.

What is claimed is:

1. A device for measuring an odor, the device comprising:
a prechamber comprising an inlet and an outlet provided in respective end portions thereof;
a flow guide pipe disposed in the prechamber and connected between the inlet and the outlet in a predetermined pattern to allow air containing the odor to flow therethrough;
a first sensor mounted to the inlet, the first sensor being configured to measure a temperature and a humidity of the air entering the flow guide pipe;
a second sensor mounted to the outlet, the second sensor being configured to measure the temperature and the humidity of the air discharged from the flow guide pipe;
a first temperature/humidity controller mounted to the prechamber, the first temperature/humidity controller being configured to adjust the temperature and the humidity of the air flowing through the flow guide pipe, wherein the first temperature/humidity controller comprises:
a first heater mounted to the prechamber, the first heater being configured to heat the air flowing through the flow guide pipe in order to adjust the temperature and the humidity of the air; and
a first cooler mounted to the prechamber, the first cooler being configured to cool the air flowing through the flow guide pipe in order to adjust the temperature and the humidity of the air;
an odor sensor chamber connected to the outlet via a connection pipe; and
an odor sensor mounted in the odor sensor chamber, the odor sensor being configured to sense the odor contained in the air discharged from the flow guide pipe.

2. The device of claim 1, further comprising a controller configured to determine a need for a heating operation or a cooling operation of the first temperature/humidity controller based on the temperature and the humidity of the air measured by the first sensor and the temperature and the humidity of the air measured by the second sensor.

3. The device of claim 2, wherein the controller is configured to control the first temperature/humidity controller to perform the heating operation in response to a determination that the temperature of the air measured by the first sensor is less than a first reference value or the humidity of the air measured by the first sensor is equal to or greater than a second reference value and to control the first temperature/humidity controller to perform the cooling operation in response to a determination that the temperature of the air measured by the first sensor is equal to or greater than the first reference value or the humidity of the air measured by the first sensor is less than the second reference value.

4. The device of claim 2, wherein the controller is configured to control the first temperature/humidity controller to stop the heating operation or the cooling operation in response to a determination that the temperature of the air and the humidity of the air measured by the second sensor have reached respective reference values.

5. The device of claim 1, wherein the first temperature/humidity controller comprises a Peltier element mounted to the prechamber to heat or cool the air flowing through the flow guide pipe in order to adjust the temperature and the humidity of the air.

6. The device of claim 1, wherein the predetermined pattern of the flow guide pipe connected between the inlet and the outlet is a helical pattern, a zigzag pattern, or a spiral pattern in order to secure a heating time or a cooling time for adjustment of the temperature and the humidity of the air.

7. The device of claim 1, wherein:
the flow guide pipe comprises a first flow guide pipe and a second flow guide pipe; and
the first flow guide pipe and the second flow guide pipe are independently connected between the inlet and the outlet in order to secure a heating time or a cooling time for adjustment of the temperature and the humidity of the air.

8. The device of claim 1, further comprising a second temperature/humidity controller mounted to the odor sensor chamber, the second temperature/humidity controller being configured to secondarily adjust the temperature and the humidity of the air introduced into the odor sensor chamber in response to a first control signal of a controller.

9. The device of claim 8, wherein the controller is configured to control the second temperature/humidity controller to perform a heating operation or a cooling operation in order to secondarily adjust the temperature and the humidity of the air introduced into the odor sensor chamber in response to a determination that the temperature and the humidity of the air measured by the second sensor have not reached respective reference values.

10. The device of claim 8, wherein the second temperature/humidity controller comprises:
a second heater mounted to the odor sensor chamber, the second heater being configured to heat the air introduced into the odor sensor chamber in order to adjust the temperature and the humidity of the air in response to a second control signal of the controller; and
a second cooler mounted to the odor sensor chamber, the second cooler being configured to cool the air introduced into the odor sensor chamber in order to adjust the temperature and the humidity of the air in response to a third control signal of the controller.

11. The device of claim 1, wherein the odor sensor chamber comprises a first odor sensor chamber and a second odor sensor chamber that are independently connected to the outlet via branch pipes.

12. A method of measuring an odor, the method comprising:
causing air containing the odor to flow to a flow guide pipe connected between an inlet and an outlet of a prechamber;
measuring, by a first sensor mounted to the inlet and a second sensor mounted to the outlet, a temperature and a humidity of the air;
controlling, by a controller, a first temperature/humidity controller mounted to the prechamber to perform a heating operation or a cooling operation based on the temperature and the humidity of the air measured by each of the first sensor and the second sensor;
adjusting the temperature and the humidity of the air flowing through the flow guide pipe to reference values through the heating operation or the cooling operation of the first temperature/humidity controller, wherein the first temperature/humidity controller comprises:
a first heater mounted to the prechamber, the first heater being configured to heat the air flowing through the flow guide pipe in order to adjust the temperature and the humidity of the air; and
a first cooler mounted to the prechamber, the first cooler being configured to cool the air flowing through the flow guide pipe in order to adjust the temperature and the humidity of the air;
supplying the air adjusted in the temperature and the humidity to an interior of an odor sensor chamber connected to the outlet; and
sensing, by an odor sensor mounted in the odor sensor chamber, the odor contained in the air introduced into the odor sensor chamber.

13. The method of claim 12, wherein the controller controls the first temperature/humidity controller to perform the heating operation in response to a determination that the temperature of the air measured by the first sensor is less than a first reference value or the humidity of the air measured by the first sensor is equal to or greater than a second reference value.

14. The method of claim 12, wherein the controller controls the first temperature/humidity controller to perform the cooling operation in response to a determination that the temperature of the air measured by the first sensor is equal to or greater than a first reference value or the humidity of the air measured by the first sensor is less than a second reference value.

15. The method of claim 12, further comprising controlling the first temperature/humidity controller to stop the heating operation or the cooling operation in response to a determination that the temperature and the humidity of the air measured by the second sensor have reached respective reference values.

16. The method of claim 12, further comprising controlling a second temperature/humidity controller mounted to the odor sensor chamber to perform the heating operation or the cooling operation in order to secondarily adjust the temperature and the humidity of the air introduced into the odor sensor chamber in response to a determination that the temperature and the humidity of the air measured by the second sensor have not reached respective reference values.

17. The method of claim 12, wherein the flow guide pipe is connected between the inlet and the outlet in a helical pattern, a zigzag pattern, or a spiral pattern in order to secure a heating time or a cooling time for adjustment of the temperature and the humidity of the air flowing through the flow guide pipe.

18. The method of claim 12, wherein the first temperature/humidity controller comprises a Peltier element mounted to the prechamber, the Peltier element performing the heating operation by emitting heat to increase the temperature of the air in the flow guide pipe and lower the humidity thereof, and performing the cooling operation by absorbing heat to lower the temperature of the air in the flow guide pipe and increase the humidity thereof.

19. The method of claim 12, wherein supplying the air adjusted in the temperature and the humidity comprises supplying the air to a first odor sensor chamber and a second odor sensor chamber that are independently connected to the outlet via branch pipes, and wherein sensing the odor comprises sensing, by respective odor sensors mounted in the first odor sensor chamber and the second odor sensor chamber, the odor contained in the air introduced into each of the first odor sensor chamber and the second odor sensor chamber.

20. A device for measuring an odor, the device comprising:

a prechamber comprising an inlet and an outlet provided in respective end portions thereof;

a flow guide pipe disposed in the prechamber and connected between the inlet and the outlet in a predetermined pattern to allow air containing the odor to flow therethrough;

a first sensor mounted to the inlet, the first sensor being configured to measure a temperature and a humidity of the air entering the flow guide pipe;

a second sensor mounted to the outlet, the second sensor being configured to measure the temperature and the humidity of the air discharged from the flow guide pipe;

a first temperature/humidity controller mounted to the prechamber, the first temperature/humidity controller being configured to adjust the temperature and the humidity of the air flowing through the flow guide pipe;

an odor sensor chamber connected to the outlet via a connection pipe; and an odor sensor mounted in the odor sensor chamber, the odor sensor being configured to sense the odor contained in the air discharged from the flow guide pipe, wherein the predetermined pattern of the flow guide pipe connected between the inlet and the outlet is a helical pattern, a zigzag pattern, or a spiral pattern in order to secure a heating time or a cooling time for adjustment of the temperature and the humidity of the air.

\* \* \* \* \*